United States Patent [19]

Burrell et al.

[11] Patent Number: 5,387,756
[45] Date of Patent: Feb. 7, 1995

[54] MODIFICATION OF PLANT METABOLISM

[76] Inventors: Michael M. Burrell; Keith S. Blundy, both c/o Advanced Technologies (Cambridge) Limited, Cambridge Science Park, Cambridge, England

[21] Appl. No.: 991,451

[22] Filed: Dec. 16, 1992

Related U.S. Application Data

[63] Continuation of Ser. No. 628,216, Dec. 17, 1990, abandoned.

[30] Foreign Application Priority Data

Dec. 21, 1989 [GB] United Kingdom ............... 8928937
Jul. 6, 1990 [GB] United Kingdom ............... 9014988

[51] Int. Cl.$^6$ ................. A01H 1/04; C12N 9/12; C12N 15/00
[52] U.S. Cl. ................. 800/205; 800/DIG. 42; 435/69.1; 435/70.1; 435/172.3; 435/194
[58] Field of Search .......... 435/69.1, 70.1, 172.3, 435/183, 240.4, 320.1, 194; 800/205, 250, 255, DIG. 42; 536/23.2, 23.6, 23.7

[56] References Cited

U.S. PATENT DOCUMENTS 4,801,540 1/1989 Hiatt et al. ................ 435/172.3

FOREIGN PATENT DOCUMENTS 8809334 12/1988 WIPO .............. C07H 15/12
8908145 9/1989 WIPO .............. C12N 15/00

OTHER PUBLICATIONS von Schaewen et al. 1990. EMBO J 9(10):3033–3044.
Hellinga et al. 1985. Eur. J. Biochem. 149:363–373.
Yang et al. 1989. Plant Science 64(1):99–111.
Khursheed et al. 1988. J. Biol. Chem. 263(35):18953–18960.
Gay et al. 1983. J. Bacteriol. 153(3):1424–1431.
Ap–Rees et al. 1988. Symp. Soc. Exp. Biol. 42:377–393.
Twell et al. 1987. Plant Mol. Biol. 9:365–375.

*Primary Examiner*—David T. Fox

[57] ABSTRACT

A transgenic plant is prepared by a method in which a plant cell is transformed with a chimaeric gene comprising a promoter and a gene encoding a polypeptide which displays the activity of an enzyme which regulates the amount of a metabolic intermediate in glycolysis or in a pathway for the synthesis or degradation of starch, sucrose or reducing sugar from a glycotyltic intermediate.

In stored potatoes the subject of the invention an increased level of phosphofructokinase results in reduced accumulations of sugars in the tubers.

1 Claim, 3 Drawing Sheets a - Phosphofructokinase
b - Pyruvate kinase
c - Invertase
d - Starch synthase
e - Adenine diphosphoglucose pyrophosphorylase
f - Sucrose synthase
g - 6 phosphofructokinase (pyrophosphate)
h - Sucrose phosphate synthase.

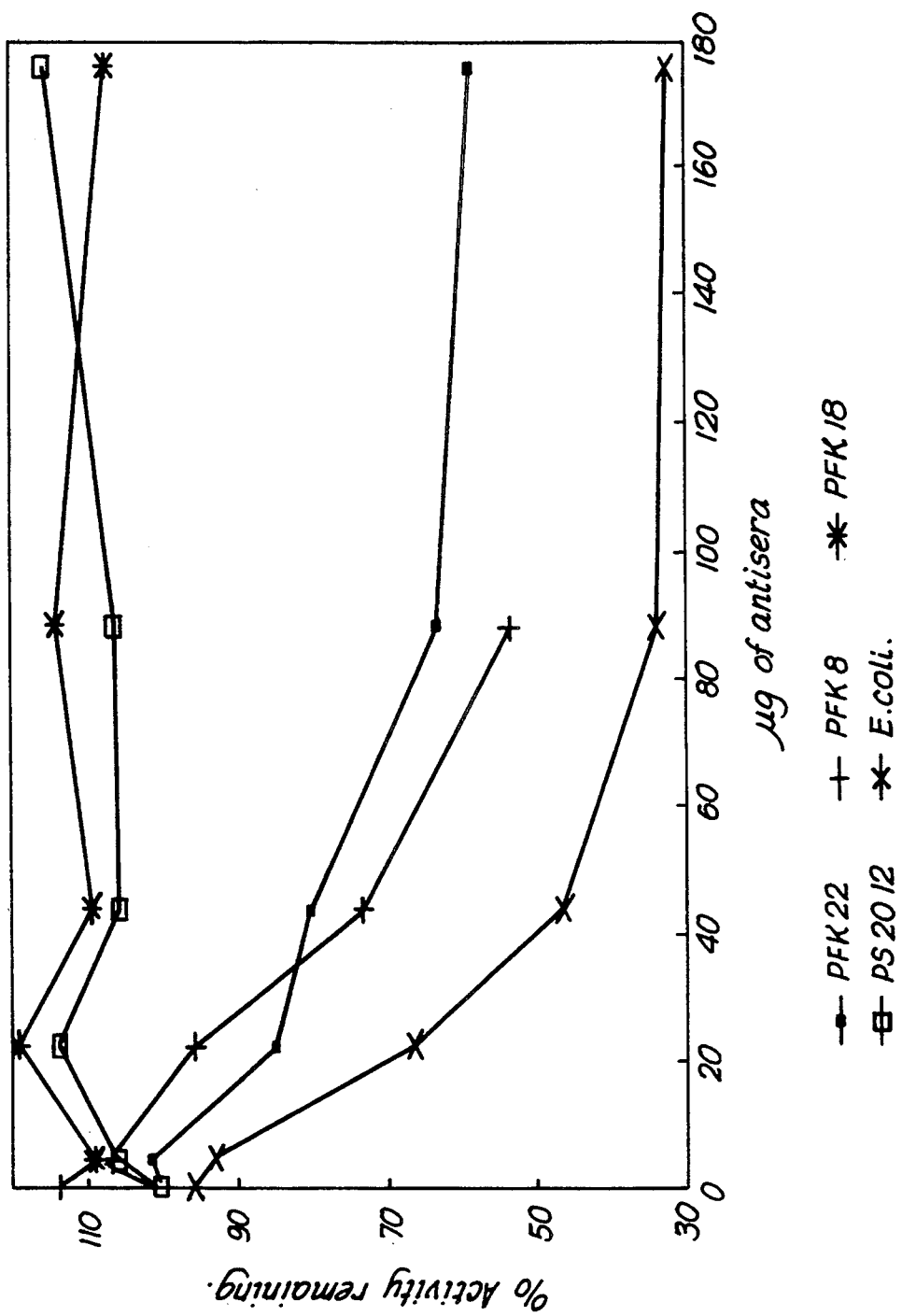

MODIFICATION OF PLANT METABOLISM

This is a continuation of copending application Ser. No. 07/628,216 filed on Dec. 17, 1990.

BACKGROUND OF THE INVENTION

The present invention relates to transgenic plants and their preparation.

BRIEF DESCRIPTION OF THE RELATED ART

Phosphofructokinase (PFK :EC 2.7.1.11) is widely regarded as a key regulatory enzyme controlling the entry of carbon into glycolysis. Glycolysis, especially in plant cells, serves to supply both respiratory carbon for energy production and intermediates for other metabolic pathways. The potato tuber contains four forms of PFK (Kruger et al, Arch. Biochem. Biophys. 267, 690–700) and pyrophosphate fructose-6-phosphate phosphotransferase (PFP: EC 2.7.1.90) which can catalyse the conversion of fructose-6-phosphate to fructose-1, 6-bisphosphate. PFK is present in both the cytosol and the amyloplast while PFP is only known to occur in the cytosol.

It has previously been thought that PFK alone controls the total glycolytic flux. However, we have now found that this is not the case. We introduced additional PFK into potato plants by genetic manipulation. Our results indicate that a substantial increase in PFK activity did not substantially alter flux through glycolysis but changed the pool sizes of intermediates. The results indicate that regulation of glycolytic flux may be achieved not only at the entry of carbon into the pathway but also exit from it. This finding has general applicability.

SUMMARY OF THE INVENTION

Accordingly, the present invention provides a process for the preparation of a transgenic plant, which method comprises:

(i) transforming a plant cell with a chimaeric gene comprising (a) a suitable promoter and (b) a coding sequence the product of which causes modification of the amount of metabolic intermediate in glycolysis or in a pathway for the synthesis or degradation of starch, sucrose or reducing sugar; and (ii) regenerating a plant from the transformed cell.

The invention also provides the chimaeric gene. A vector suitable for use in the present process comprises the chimaeric gene such that the chimaeric gene is capable of being expressed in a plant cell transformed with a vector. A plant cell according to the invention therefore harbours the chimaeric gene such that the chimaeric gene is capable of being expressed therein.

A transgenic plant can therefore be obtained which harbours in its cells the chimaeric gene such that the chimaeric gene is capable of being expressed in the cells of the plant. Seed or other propagules can be obtained from the transgenic plant and used to grow further plants stably transformed with the chimaeric gene.

BRIEF DESCRIPTION OF THE DRAWINGS

In FIG. 1 the broken lines indicate tentatively assumed pathways.

FIG. 3 shows the immunodetection of $E.$ $coli$ PFK activity. PFK was immunoactivated with antisera raised to the introduced $E.$ $coli$ PFK. Antisera was mixed with equal amounts of PFK activity (1 nmole F6P consumed min$^{-1}$) from two transgenic lines expressing PFK (PFK22, O; PFK8,+), two transgenic lines one not expressing PFK (PFK16*) and expressing GUS (PS20-12), or $E.$ $coli$ PFK (x). Bound PFK was removed with protein A and the activity not removed assayed (Kruger et al), Archives of Biochemistry and Biophysics 267 690–700, 1989.

DETAILED DESCRIPTION OF THE PREFERRED EMBODIMENTS OF THE INVENTION

Figure 1:
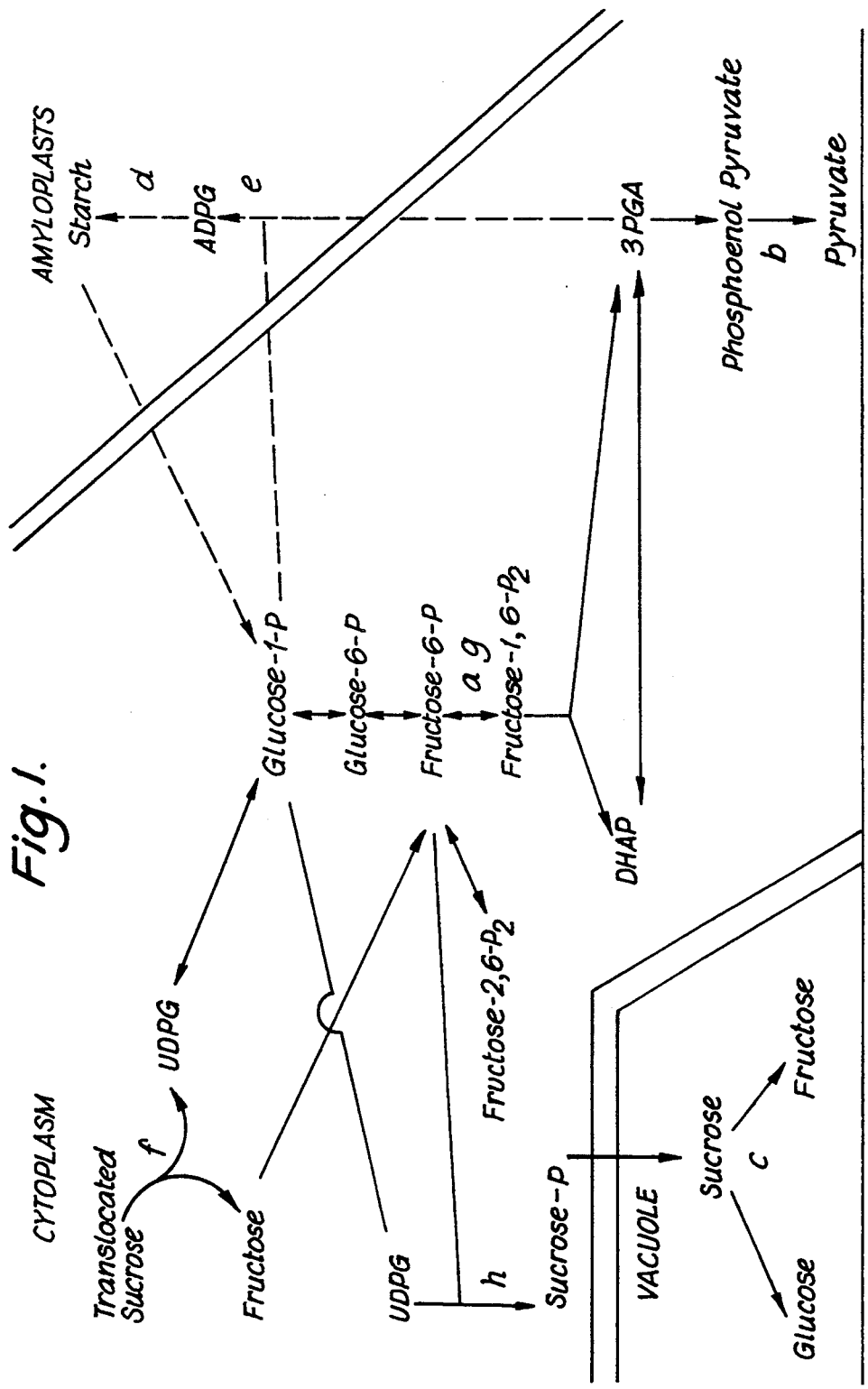
FIG. 1 shows a simplified diagram of carbohydrate metabolism with reference to plant storage tissues such, for example, as potato tubers.

The invention enables plant metabolism to be altered in a glycolytic pathway or in a pathway for the synthesis or degradation of starch, sucrose or a reducing sugar such as glucose or fructose. It enables the accumulation of pathway metabolites to be altered. Several applicable pathways are shown in FIG. 1 of the accompanying drawings.

The invention is particularly applicable to potatoes. It had been expected that the introduction and expression of additional PFK into potato tuber cells would cause a high flux in the glycolytic pathway. Furthermore, if this gene had been introduced and expressed in the whole plant, it would not have been unreasonable to have expected that the plant would have died. In the event, though, it was surprising to find that after the introduction and expression of the PFK gene the plant did not die and the flux in the glycolysis metabolism pathway was not increased.

The storage of potato tubers in low temperature storage conditions normally results in less PFK activity. This, it is believed, leads to an increased production in the potato tubers of sucrose and reducing sugars. The accumulation of these sugars in the potato tubers presents a significant problem to processors of potatoes. For example, producers of crisps and chips (otherwise known respectively as potato chips and French fries) have found that the presence of an increased level of sugars tends to cause an undue browning of the products during the frying process.

When potato tubers of the subject invention are stored at low temperatures, the increased amount of PFK present therein ensures a continued flux into the glycolysis metabolism pathway. This in turn means that the flux level in the sucrose synthesis pathway is lower than has heretofore been the case with stored potato tubers. Thus significantly reduced levels of sucrose and reducing sugars accumulates in the stored tubers.

In the invention, a chimaeric gene is constructed which comprises (a) a suitable promoter operably linked to (b) a coding sequence the product of which causes modification of the amount of a metabolic intermediate in glycolysis or in a pathway for the synthesis or degradation of starch, sucrose or reducing sugar. The chimaeric gene may be constructed in any convenient fashion. The coding sequence is provided such that it is expressible in plant cells.

The promoter (a) should be capable of expressing the coding sequence of interest in a plant. The promoter may be a promoter capable of directing expression in a particular tissue of a plant and/or at particular stages of development. The promoter may be heterologous or homologous to the plant. A suitable promoter may be the 35S cauliflower mosaic virus promoter, a nopaline synthase or octopine synthase promoter, a patatin promoter or a small sub-unit of rubisco. A promoter from tubers, e.g. patatin, is preferred for directing expression in potatoes, in particular potato tubers. A suitable promoter may be, for example, a constitutive promoter or a tissue-specific promoter.

The coding sequence (b) can encode an enzyme which regulates the amount of a metabolic intermediate of a specific pathway. The pathway may be the glycolytic pathway. Glycolysis is the sequence of reactions which converts glucose to pyruvate with concomitant production of ATP or NADH and is also termed the Embden-Meyerhof-Parnas pathway.

Sucrose consists of glucose and fructose coupled via an alpha 1-2 O-glycosidic bond. Pathways of sucrose synthesis therefore involve enzyme steps that produce suitable intermediates to form this linkage. Starch is a polymer which consists mainly of alpha 1-4 linked glucose with varying amounts of 1-6 linked glucose. Thus pathways of starch synthesis involve steps that produce suitable intermediates to form this polymer.

A coding sequence is selected which when expressed in plant cells will increase or decrease the metabolism of a pathway mentioned above. The coding sequence (b) may encode for a pathway enzyme or an active modified form of a pathway enzyme, for example a truncated pathway enzyme. The pathway enzyme may be, for example, PFK (EC 2.7.1.11), pyruvate kinase (PK) (EC 2.7.1.40), acid invertase (EC 3.2.1.26), starch synthase (EC 2.4.1.21), adenine diphosphoglucose pyrophosphorylase (EC 2.7.7.27), sucrose synthase (EC 2.4.1.13), 6-phosphofructokinase (pyrophosphate) (EC 2.7.1.90) or sucrose phosphate synthetase (SPS) (EC 2.4.1.14).

The coding sequence may be from a plant gene or a non-plant gene such as a microbial gene. It may be from a bacterial gene, for example a gene from *E. coli*, or a yeast gene, for example *Saccharomyces cerevisiae*. In particular, a PFK coding sequence may be provided by the pfkA gene from *E. coli* or by a pfk gene from *Solanum tuberosum*. An acid invertase coding sequence may be provided from *Saccharomyces cerevisiae*.

Plant cells can be transformed with the chimaeric gene by direct DNA uptake, typically by way of a DNA fragment comprising the chimaeric gene. Alternatively, there may be used a vector incorporating the chimaeric gene. The chimaeric gene typically includes transcriptional control sequences, for example a promoter as above, and translational initiation and/or termination sequences. Plant terminator and polyadenylation sequences may be present. A vector typically contains too a region which enables the chimaeric gene to be transferred to and stably integrated in the plant cell genome.

The vector is therefore typically provided with transcriptional regulatory sequences and/or, if not present at the 3'-end of the coding sequence of the gene, a stop codon. A DNA fragment may therefore also incorporate a terminator sequence and other sequences which are capable of enabling the gene to be expressed in plant cells. An enhancer or other element able to increase or decrease levels of expression obtained in particular parts of a plant or under certain conditions, may be provided in the DNA fragment and/or vector. The vector is also typically provided with an antibiotic resistance gene which confers resistance on transformed plant cells, allowing transformed cells, tissues and plants to be selected by growth on appropriate media containing the antibiotic.

Transformed plant cells can be selected by growth in an appropriate medium. Plant tissue can therefore be obtained comprising a plant cell which harbours a gene encoding an enzyme under the control of a promoter, for example in the plant cell genome. The gene is therefore expressible in the plant cell. Plants can then be regenerated which include the gene and the promoter in their cells, for example integrated in the plant cell genome such that the gene can be expressed. The regenerated plants can be reproduced and, for example, seed obtained.

A preferred way of transforming a plant cell is to use *Agrobacterium tumefaciens* containing a vector comprising a chimaeric gene as above. A hybrid plasmid vector may therefore be employed which comprises:

(a) a chimaeric gene containing regulatory elements capable of enabling the gene to be expressed when integrated in the genome of a plant cell;

(b) at least one DNA sequence which delineates the DNA to be integrated into the plant genome; and (c) a DNA sequence which enables this DNA to be transferred to the plant genome.

Typically the DNA to be integrated into the plant cell genome is delineated by the T-DNA border sequences of a Ti-plasmid. If only one border sequence is present, it is preferably the right border sequence. The DNA sequence which enables the DNA to be transferred to the plant cell genome is generally the virulence (vir) region of a Ti-plasmid.

The gene coding for the enzyme and its transcriptional and translational control elements can therefore be provided between the T-DNA borders of a Ti-plasmid, The plasmid may be a disarmed Ti-plasmid from which the genes for tumorigenicity have been deleted. The gene and its transcriptional control elements can, however, be provided between T-DNA borders in a binary vector in trans with a Ti-plasmid with a vir region. Such a binary vector therefore comprises:

(a) the chimaeric gene under the control of regulatory elements capable of enabling the gene to be expressed when integrated in the genome of a plant cell; and (b) at least one DNA sequence which delineates the DNA to be integrated into the plant genome.

*Agrobacterium tumefaciens*, therefore, containing a hybrid plasmid vector or a binary vector in trans with a Ti-plasmid possessing a vir region can be used to transform plant cells. Tissue explants such as stems or leaf discs may be inoculated with the bacterium. Alternatively, the bacterium may be co-cultured with regenerating plant protoplasts. Plant protoplasts may also be transformed by direct introduction of DNA fragments which encode the enzyme and in which the appropriate transcriptional and translational control elements are present or by a vector incorporating such a fragment. Direct introduction may be achieved using electroporation, polyethylene glycol, microinjection or particle bombardment.

Plant cells from angiospermous, gymnospermous, monocotyledonous or dicotyledonous plants can be transformed according to the present invention. Monocotyledonous species include barley, wheat, maize and rice. Dicotyledonous species include cotton, lettuce, melon, pea, petunia, potato, rape, soyabean, sugar beet, sunflower, tobacco and tomato. Potato cultivars to which the invention is applicable include Desiree, Marls Bard, Record and Russet Burbank.

Tissue cultures of transformed plant cells are propagated to regenerate differentiated transformed whole plants. The transformed plant cells may be cultured on a suitable medium, preferably a selectable growth medium. Plants may be regenerated from the resulting callus. Transgenic plants are thereby obtained whose cells incorporate the chimaeric gene in their genome, the chimaeric gene being expressible in the cells of the plants. Seed or other propagules from the regenerated plants can be collected for future use.

A preferred procedure in respect of the potato variety Record is as follows.

Plant Material

Record shoot cultures are maintained in vitro on Murashige and Skoog (MS) medium in Magenta GA-7 containers at 22° C. (16h/8h light/dark). These are nodally sub-cultured every 3 weeks.

In vitro shoots of 2-3 inches (5-7.5 cm) height are potted in 2.5 inches (6.4 cm) pots of Levingtons F1 compost. They are weaned in a propagator for one week in a growth room at 18° C. (16h/8h light/dark). The propagator is removed and the plants repotted at 3 weeks into 5 inch (12.7 cm) pots. At 5-7 weeks the plants are used for transformation.

*Agrobacterium tumefaciens*

Liquid overnight cultures of suitable strains e.g. LBA4404, C58#3 are grown at 28° C. to an $OD_{600}$ of 0.8 in L-broth (see appendix).

Cocultivation

The youngest four most expanded leaves are taken and surface sterilised in 10% Domestos ( commercial bleach) for 15 minutes. Leaves are rinsed thoroughly with sterile water and then cut into discs with a 7 mm cork borer. The discs are mixed with the Agrobacterium for 1-5 minutes, blotted dry on filter paper (Whatman No. 1) and then placed on callusing medium (see appendix) in 90 mm triple vented petri dishes, lower epidermis down. The 90 mm triple vented petri dishes are sealed with tape, cut to allow gas exchange and then incubated at 22° C./ (16h/8h light/dark). The discs are transferred to callusing medium plus 500 µg ml$^{-1}$ of claforan and 30 µg ml$^{-1}$ kanamycin after 48 hours. This removes bacteria and selects for transformed cells.

Regeneration of Transformed Shoots

After 1 week, the discs are transferred to shooting medium (see appendix) containing the same antibiotics. Further transfers are made onto the same medium until shoots can be excised (usually about 4 weeks). Shoots with calli are transferred to MS medium with cefotaxime in well ventilated containers, e.g. Magenta. Transformants are maintained, after several passages with cefotaxime to remove bacteria, on MS medium. They may be removed from in vitro, weaned and grown to maturity as described for the stock plants. The process yields transformed Record plants at a frequency of up to 30% Of the discs cocultivated.

Appendix

| | |
|---|---|
| L-broth | 10 g l$^{-1}$ *bacotryptone* |
| | 5 g l$^{-1}$ *yeast extract* |
| | 5 g l$^{-1}$ *sodium chloride* |
| | 1 g l$^{-1}$ *glucose* |
| Callusing medium | MS with 3% sucrose |
| | 0.5 mg l$^{-1}$ 2,4-D |
| | 2.5 mg l$^{-1}$ BAP |
| Shooting medium | MS plus 3% sucrose |
| | 2.5 mg l$^{-1}$ BAP |
| | 1.0 mg l$^{-1}$ GA$_3$ |

The following examples illustrate the invention.

EXAMPLE 1: Production of PFK in potato tubers

Figure 2:
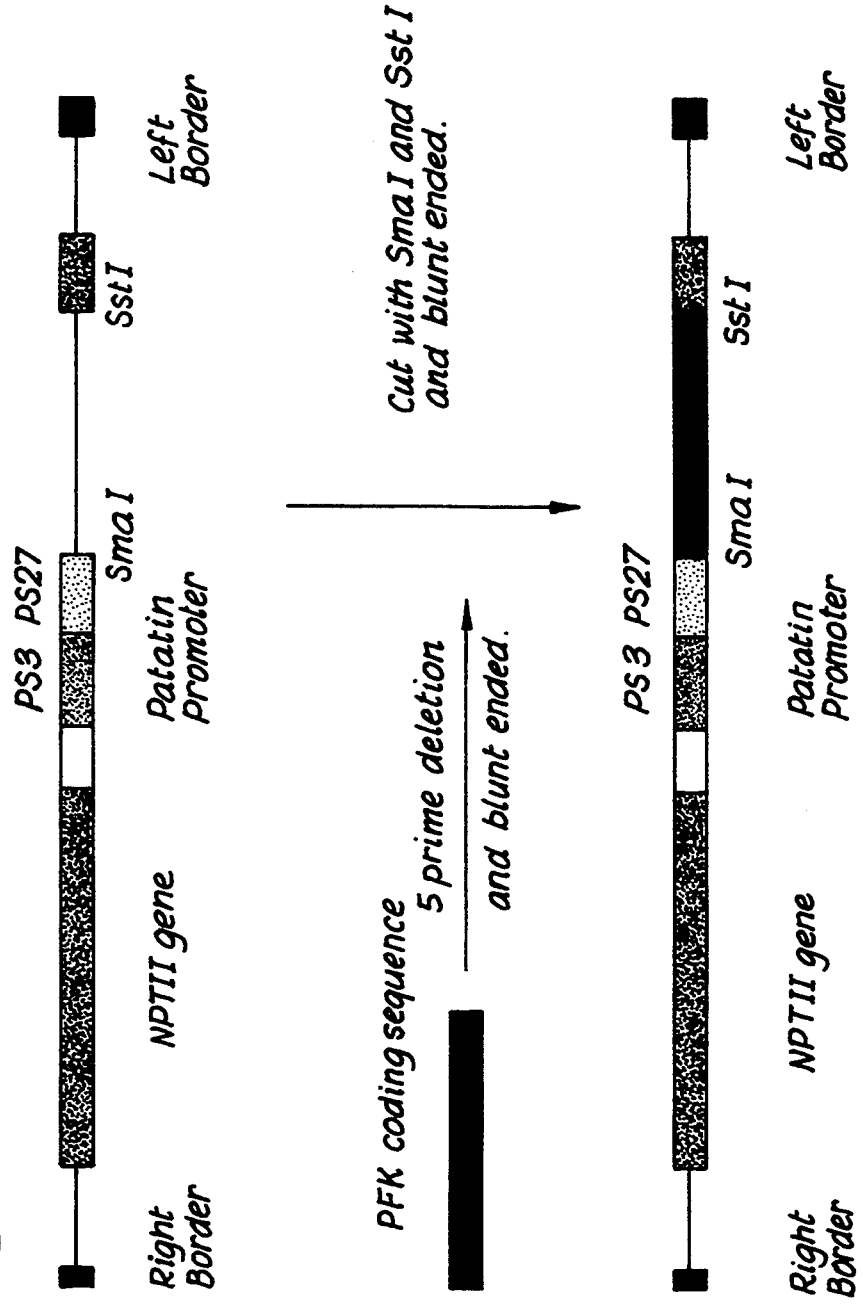
FIG. 2 shows the procedure used to produce a chimaeric PFK gene.

The procedure used to produce a chimaeric PFK gene to provide tuber-specific expression of PFK is illustrated in FIG. 2. The PFK coding sequence was obtained from a clone of the pfkA gene as described by Hellinga H.W. and Evans P.R. (Eur. J. Biochem 149 363-373, 1985). The PFK coding sequence was isolated so that only 20 base pairs remained before the translational start site. More specifically the *E. coli* pfkA gene on plasmid pHE1012 was deleted at the 5' end to 20 bp from the translational start site and 50 bp from the 3' end of the coding sequence. This was then blunt end ligated into the plasmid pFW4101 in place of the GUS (β-glucuronidase) coding sequence to give plasmid pFW4023. pFW4101 was constructed with a patetin promoter made from two genomic clones PS3 and PS27. The patatin fragments PS3 and PS27 were derived from the genomic clones described by Mignery et al (Gene 62, 27-44, 1988). The fragments consist of −3.5 kb to −1 kb of PS3 and −1 kb to +3 kb of PS27 numbered in relation to the translation start.

*E. coli* herbcuring pFW4023 and *E. coli* herbcuring pFW4101 were deposited at the National Collection of Industrial and Marine Bacteria, Aberdeen, GB on 5 July 1990 under accession numbers NCIMB 40305 and NCIMB 40306.

The vectors pFW4101 and pFW4023 were transferred separately into *Agrobacterium tumfacines* strain LBA 4404 by triparental mating. The Agobacterium strains were used to transform the potato cultivar Desires. A large family or over 60 transgenic plants were produced. Southern analysis showed that the plants contained between one and eight copies of the *E. coli* pfkA gene. Some of these plants produced tubers which contained considerable PFK activity. PFK activity was measured as described by Kruger et al, Archives of Biochemistry and Biophysics 267 690-700, 1988. Intermediates were extracted with ice cold perchlorate and measured enzymatically. The results are shown in Table 1.

TABLE 1

| PFK Activity and amount of glycolytic intermediates | | | | | | |
|---|---|---|---|---|---|---|
| | PFK transgenic | | GUS transgenic | | | |
| | mean | (SD) | mean | (SD) | t value | P |
| PFK activity[1] | 625 | (206) | 29 | (12) | 4.07 | >99 |
| Glc-6p[2] | 78 | (8.9) | 100 | (21) | 1.97 | >95 |
| Fru-6p[2] | 21 | (4.2) | 29 | (9) | 1.77 | >90 |
| Ratio | 3.7 | (0.56) | 3.7 | (0.66) | 0.09 | N.S. |
| PEP[2] | 82 | (20.4) | 28 | (8.0) | 3.54 | >99 |
| Pyr[2] | 44 | (22.6) | 37 | (16) | 0.80 | N.S. |
| Ratio | 2.5 | (1.3) | 1.0 | (0.6) | 2.20 | >95 |

[1]PFK activity is given as nmoles min$^{-1}$ g fr. wt.$^{-1}$.
[2]Intermediates are given as nmoles g fr. wt.$^{-1}$.

Assays containing mixtures of extracts from two plants differing in amount of activity did not reveal the presence of activators or inhibitors (data not shown). Two lines of evidence were sought to demonstrate that the observed increase in PFK activity was due to *E. coli*

PFK. Firstly antisera raised to this enzyme was used to immunoinactivate specifically the *E. coli* PFK activity in crude protein extracts from tubers. The results are shown in FIG. 3. A considerable proportion of the activity could be removed in lines showing increased activity but not in lines expressing GUS or not showing elevated activity (FIG. 3). Mixtures of line 12 (GUS) control plants with either *E. coli* PFK or line 22 (elevated PFK) gave the expected results indicating that the immunoinactivation was not due to inhibitors in the control plants. Secondly the antisera was used with Western blots to show clearly the appearance of the 36 kD *E. coli* PFK polypeptide of the correct molecular weight (data not shown). This band does not coincide with any predominant potato protein (data not shown) or potato PFK which has subunit molecular weights between 55 and 63 kD.

To discover whether this increase in enzyme activity, which in the strongest expressing tissue was 40 fold, had altered glycolytic flux we initially measured the rate of respiration by Warburg manometry. Respiratory rates were determined by Warburg manometry (Umbreit). Tubers were bathed in 2.7 ml of 20 mM phosphate buffer pH5.2 containing 0.5 mM glucose. $CO_2$ was absorbed in 10% KOH. These results are shown in Table 2.

TABLE 2

| | Respiration in Tubers | | | |
|---|---|---|---|---|
| | Gas exchange nmol $min^{-1} g^{-1}$ fr. wt. (S.D.) | | | |
| | PFK Transgenic | | GUS Transgenic | |
| Oxygen Uptake | | | | |
| at 2 h | 29.4 | (8.9) | 36.3 | (7.2) |
| at 5 h | 49.8 | (4.1) | 55.2 | (10.4) |
| $CO_2$ release | | | | |
| at 2 h | 22.2 | (3.2) | 24.3 | (8.6) |
| at 5 h | 33.7 | (7.7) | 44.0 | (9.0) |

There was no indication of a change in oxygen uptake or carbon dioxide evolution. Thus if respiration determined by gas exchange is an indication of glycolytic flux, excess PFK has not altered it. However in these tubers it is possible that a substantial amount of the respired carbohydrate entered the citric acid cycle via the pentose phosphate pathway and not glycolysis. Both pathways consume glucose-6-P. If this were the case then the addition of a large excess of PFK might change the distribution of metabolism but not the overall flux.

We therefore determined the rate of release of $^{14}CO_2$ from 6$^{14}$C-glucose and from 1-$^{14}$C-glucose. The ratio of release 6C/1C indicates the contribution of glycolysis to respiration. In both PFK and GUS transgenic plants the ratio was approximately 0.2 after 40 mins of incubation in $^{14}$C-glucose, 0.3 after 2 h and 0.4 after 4 h. Thus the presence of up to 40 fold excess of PFK activity has not altered the relative contributions of glycolysis and pentose phosphate pathway to glycolytic flux.

These results suggest that PFK is not regulating the entry of carbon into glycolysis in potato tubers. We therefore measured the amounts of glucose-6-P, and fructose-6-P, phosphoenol pyruvate (PEP) and pyruvate (Table 1). Elevated PFK activity has clearly lowered the amount of hexose-phosphate present but the mass action ratio (Glc-6P:Fru-6P) has remained the same and is approximately 4. This is near the equilibrium constant of glucose-6-phosphate isomerase (Sicher and Kremer, Pl. Science 67, 47–56, 1990). More notable however is the large increase in PEP and change in the ratio of PEP:pyruvate. This strongly suggests that the increased level of PFK has led to more carbon entering glycolysis for a given respiratory flux and in those plants where PFK activity is increased the enzymes (probably pyruvate kinase and PEP carboxylase) that use PEP are strongly influencing the flux.

Plants of cv Desiree transformed as described above were grown in the field and the amount of sucrose in the potato tubers measured at harvest was less in lines expressing high PFK. The difference between sucrose content is significant at P=0.05. Thus this modification of glycolysis can cause an alteration in a pool of metabolite in a related pathway of carbohydrate metabolism (as illustrated in FIG. 1).

TABLE 3

| Alteration in sucrose content of tubers | | |
|---|---|---|
| Line | PFK Activity nmol $min^{-1} g^{-1}$ fr. wt. | Sucrose content % w/w |
| PFK22 | 1011 | 0.219 |
| PFK36 | 379 | 0.293 |
| PS20-24 | 18 | 0.347 |
| PS20-6 | 18 | 0.358 |

Such alterations are not confined to potato tubers. The patatin promoter can be induced to express in leaf tissue by incubating them in a medium of sucrose (Rocha-Sosa et al (1989) EMBO J 8 23–29). Discs were cut from leaves of plants (line PFK 22) containing the chimaeric PFK gene and control plants containing the chimaeric GUS gene (line PS20-12). After incubation in the light on a medium containing 1% sucrose, to cause the expression of the PFK gene, the tissues were analysed for changes in intermediates.

The results in Table 4 show that in a tissue other than a tuber the alterations in the activity of PFK can alter metabolic intermediates.

TABLE 4

| Ratio of $\frac{\text{Amount of intermediate in line PFK-22}}{\text{Amount of intermediate in line PS20—12}}$ (S.D.) | | |
|---|---|---|
| Fru- 2,6-$P_2$ | PEP | Pyruvate |
| 2.23 ± 0.37 | 1.18 (±0.3) | 0.49 (±0.1) |

EXAMPLE 2: Expression of *E. coli* PFK in rice callus

A chimaeric gene was constructed as described in FIG. 2 but a 35S promoter replaced the patatin promoter.

This gene was used to transform rice protoplasts and the callus assayed for PFK activity. Control callus tissue had activities of up to 1500 nmol $min^{-1} g^{-1}$ fr. wt. The transformed callus had activities of 3000 nmol $min^{-1} g^{31}$ 1 fr. wt. Thus it is possible to express this chimaeric gene in monocotyledonous plants such as rice.

We claim:

1. A transgenic potato plant which harbors in its cells a chimaeric gene, which comprises;
   (a) a promoter operably linked to
   (b) a deoxgrihonucleic acid coding sequence which encodes phosphofructokinase, said gene being capable of expression in the cells of the transgenic potato plant.

* * * * *

UNITED STATES PATENT AND TRADEMARK OFFICE
CERTIFICATE OF CORRECTION

PATENT NO. : 5,387,756
DATED : February 7, 1995
INVENTOR(S) : Michael M. Burrell and Keith S. Blundy It is certified that error appears in the above-indentified patent and that said Letters Patent is hereby corrected as shown below:

Col. 8, line 4 of Claim 1; "deoxgrihonucleic" should read
-- deoxyribonucleic --

Signed and Sealed this

Twenty-seventh Day of June, 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,387,756
DATED : February 7, 1995
INVENTOR(S) : Michael M. Burrell and Keith S. Blundy It is certified that error appears in the above-indentified patent and that said Letters Patent is hereby corrected as shown below:

Col. 6, line 32; "herbcuring" should read -- harbouring --, in both instances.

Col. 6, line 39 bridging line 40; "Desires" should read -- Desiree --.

Col. 6, line 47; "1988" should read -- 1989 --.

Col. 8, line 57; "min$^{-1}$ g$^{31}$ $^{1}$ fr. wt." should read -- min$^{-1}$ g$^{-1}$ fr. wt. --

Signed and Sealed this

Twelfth Day of September, 1995

Attest:

BRUCE LEHMAN

Attesting Officer

Commissioner of Patents and Trademarks